United States Patent [19]
Dorin et al.

[11] Patent Number: 5,814,485
[45] Date of Patent: Sep. 29, 1998

[54] **PRODUCTION OF INTERFERON-β (IFN-β) IN *E. COLI***

[75] Inventors: Glenn Dorin, San Rafael; Patrick J. McAlary, San Francisco; Kathleen M. Wong, Berkeley, all of Calif.

[73] Assignee: Chiron Corporation, Emeryville, Calif.

[21] Appl. No.: 477,310

[22] Filed: Jun. 6, 1995

[51] Int. Cl.⁶ .............................. C12N 15/22; C12N 1/21
[52] U.S. Cl. .................................. 435/69.51; 435/252.33
[58] Field of Search .............................. 530/300; 435/68, 435/69.1, 69.5, 71.1, 85.1, 69.51, 252.33

[56] References Cited

U.S. PATENT DOCUMENTS

| | | |
|---|---|---|
| 4,499,188 | 2/1985 | Konrad et al. . |
| 4,518,584 | 5/1985 | Mark et al. . |
| 4,656,131 | 4/1987 | Kitano et al. .................. 435/69.51 |
| 4,656,132 | 4/1987 | Ben-Bassat et al. ................. 435/69.5 |

FOREIGN PATENT DOCUMENTS

| | | |
|---|---|---|
| 0 192 811 A1 | 9/1986 | European Pat. Off. . |
| 62-282586 A | 12/1987 | Japan . |

OTHER PUBLICATIONS

DF Mark et al. PNAS, USA 81,5662, 1984.
W Ryan et al. Ann. NY Acad. Sci. 589,91, 1990.
DW Zabriskie et al. J. Industrial Microbiology 2, 87, 1987.
Patent Abstracts of Japan, vol. 012, No. 176 (C–498), 25 May 1988.
Ausubel, et al. "Current Protocols in Molecular Biology", 1987, John Wiley & Sons. pp. 1.1.1 –1.1.3.

*Primary Examiner*—David L. Fitzgerald
*Attorney, Agent, or Firm*—Ling-Fong Chung; Donald J. Pochopien; Robert P. Blackburn

[57] ABSTRACT

Methods for the production of interferon-β polypeptides by bacterial cells, by culturing cells capable of producing IFN-β polypeptide under conditions that induce increased production of IFN-β polypeptide. Such conditions include, for example, low potassium cation concentration and/or very low sodium cation concentration and/or specific pH ranges.

10 Claims, 5 Drawing Sheets

PRODUCTION OF INTERFERON-β (IFN-β) IN E. COLI

DESCRIPTION

1. Technical Field

This invention relates to the culturing of bacteria cells to produce a desired protein. Specifically, the invention relates to a method for the production of hydrophobic polypeptides, such as interferon-β ("IFN-β") polypeptides under certain culturing parameters, such as energy source, ion concentration, temperature, and pH.

2. Background of the Invention

Recombinant production of hydrophobic polypeptides have medical and commercial uses. For example, IFN-β is the first identified effective treatment for those with MS. It is proven to reduce the number of attacks suffered by patients with relapsing and remitting multiple sclerosis ("MS"). Further, IFN-β is also being used to treat those patients with Hepatitis B or C.

The amino acid and nucleotide sequence of IFN-β are known, as shown in Tanauguichi et al., Gene 10: 11–15 (1980). Recombinant DNA technology makes it possible to produce IFN-β that is free from viruses, e.g., HIV-1, and other contaminants from human sources. By means of such technology, IFN-β can be produced by culturing a host cell transformed with an expression vector that contains a gene encoding the amino acid sequence of IFN-β. The host cell is one which can transcribe the gene and produce the desired protein. These techniques have been used to produce IFN-β in mammalian, insect, and yeast host cells as described in, for example, Mantei et al., Nature (London) 297: 128 (1982); Ohno et al., Nucl. Acid. Res. 10: 967 (1982); and Smith et al., Mol. Cell. Biol. 3: 2156 (1983); respectively. Moreover, muteins of IFN-β having improved characteristics have also been produced as described in, for example, Mark et al., U.S. Pat. No. 4,518,584.

DISCLOSURE OF THE INVENTION

It is an object of the present invention to provide a method for producing hydrophobic polypeptides, such as IFN-β polypeptides, in higher yield than with conventional techniques. It is also an object of the present invention to provide an improved method of production of recombinant polypeptide in higher yield than that produced by recombinant techniques.

Accordingly, the invention relates to an improved method for producing hydrophobic polypeptides utilizing bacterial host cells capable of producing such polypeptides. The method comprises culturing a host cell transformed with a vector comprising the hydrophobic polypeptide coding sequences under conditions effective to induce polypeptide production, where the conditions include contacting the cell with a medium comprising a low concentration of potassium cations, for example, no greater than 120 mM, and/or a very low concentration of sodium cations, for example, no greater than 40 mM.

The invention also relates to another improved method of producing hydrophobic polypeptide comprising culturing a transformed host cell at a pH between about 5.4 and about 6.6.

Further, the invention relates to a method of producing of IFN-β polypeptides in a bacterial host, such as Escherichia coli, comprising culturing the bacterial cell capable of producing IFN-β polypeptides at about 39.5° C. in a medium comprising:

(a) no greater than about 120 mM potassium cations and no greater than about 100 μM sodium cations; and (b) glycerol as an effective energy source; at a pH between about 5.4 and about 5.7.

MODES OF CARRYING OUT THE INVENTION

Figure 1:
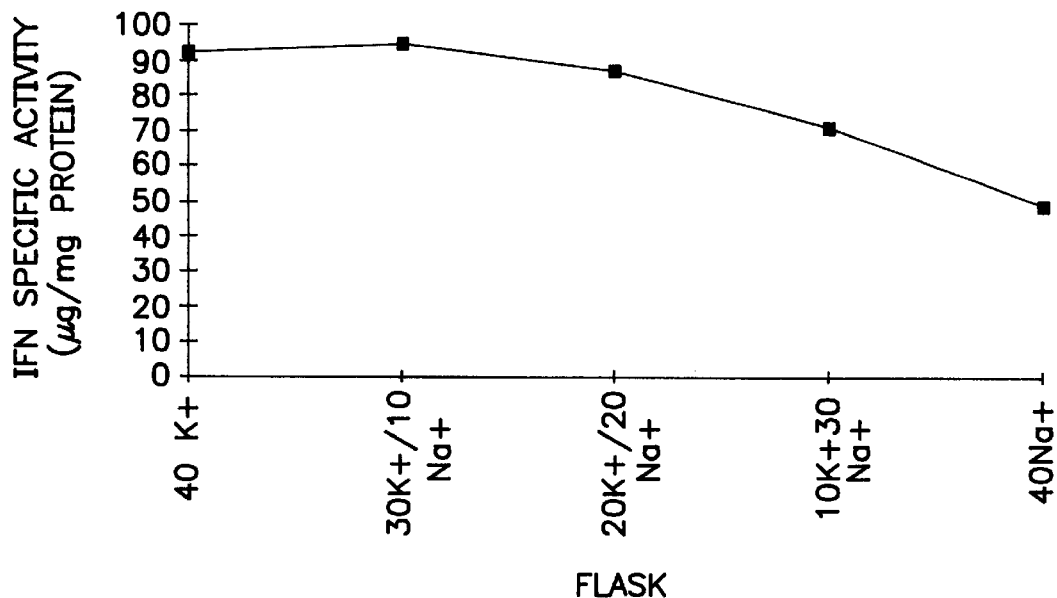
FIG. 1 shows the effect of potassium concentration on growth.

The methods of the present invention relates to culturing conditions of host cells capable of producing hydrophobic polypetides, such as IFN-β polypeptides. These conditions lead to improved cell growth and product yields.

Preferably, the host cell is transformed with an expression vector comprising the coding sequence of a hydrophobic polypeptide, an example are IFN-β polypeptide. The expression vector can also contain if desired a promoter, terminator, origin of replication, and selectable marker. These components are known in the art and can be easily assembled.

Hydrophobic polypeptides comprise an abundance of hydrophobic amino acids, such as leucine, isoleucine, phenylalanine, and valine. Hydrophobic residues comprise approximately of 20% of the total residues in a hydrophobic polypeptide; more typically, approximately of 25% of the total residues; even more typically, approximately 30%. Hydrophobic polypeptides are capable of binding to other hydrophobic substances. For example, native IFN-β binds to hydrophobic substances such as Bule Dextran, Cibacron Blue F3GA-dextran, aminobenzene bound to agarose, aminonaphthalene bound to agarose, and aminoanthracene bound to agarose, (Jankowski et al., Biochem. 15(23): 5182 (1976)). Another characteristic of hydrophobic proteins is the ratio of α helical to β-sheet residues. Hydrophobic proteins exhibit an α-helical to β-sheet ratio of approximately 2:1; more typically, a ratio of approximately 1.5:1; even more typically, approximately 1:1. The primary sequence of native IFN-β, a typical hydrophobic polypeptide, exhibits a ratio of approximately 1.1:1 according to Chou-Fasman analysis (Hayes, Biochem. Biophys. Res. Commun. 95(2): 872–879 (1980)).

With the present invention any IFN-β polypeptide can be utilized. The term "interferon-β polypeptides" or "IFN-β polypeptides" refers to native IFN-β, muteins, analogs, and derivatives thereof. Such polypeptides which exhibit either the similar biological or receptor binding activity as the native IFN-β polypeptide. All of these IFN-β polypeptides will exhibit at least 60% of the receptor binding or biological activity of the native IFN-β. More typically, the polypeptides exhibit at least 75%, even more typically the polypeptides exhibit at least 80% of the native IFN-β receptor binding or biological activity. Biological and receptor binding assays are described in Fellous et al., *Proc. Natl. Acad. Sci. USA* 79: 3082–3086 (1982); Czerniecki et al., *J. Virol.* 49(2): 490–496 (1984); Mark et al., *Proc. Natl. Acad. Sci. USA* 81: 5662–5666 (1984); Branca et al., *Nature* 294: 768–770 (1981); Williams et al., *Nature* 282: 582–586 (1979); Herberman et al., *Nature* 277: 221–223 (1979); and Anderson et al., *J. Biol. Chem.* 257(19): 11301–11304 (1982).

IFN-β polypeptides include mutants, fragments, fusions, analogs and derivatives of the native IFN-β. All of these polypeptides will exhibit some sequence identity to the native IFN-β. Human IFN-β is one example of a native IFN-β. The human amino acid sequence of such is known and is further shown in SEQ ID NO:1. The polypeptides will retain at least about 80% amino acid identity with SEQ ID NO:1; more typically, at least about 85%; even more typically, at least about 90%.

The desired hydrophobic polypeptide can be constructed from known native sequences. For example, native IFN-β can be mutated to remove the cysteine that does not participate in disulfide bonding can be mutated to a serine using in vitro mutagenesis techniques. Such mutagenesis is described in Mark et al., U.S. Pat. No. 4,518,584. Other techniques for constructing fragments, fusion, analogs, and other derivatives are described in, for example, Sambrook et al., "Molecular Cloning: A Laboratory Manual" (New York, Cold Spring Harbor Laboratory, 1989).

Once the expression vector is constructed, it can be transformed into a number of host cells, both bacterial and yeast cells. For example, transformation techniques for the following bacterial host are, for example: Masson et al. (1989) *FEMS Microbiol. Lett.* 60:273; Palva et al. (1982) *Proc. Natl. Acad. Sci. USA* 79:5582; EP Publ. Nos. 036 259 and 063 953; PCT WO 84/04541 for Bacillus; and Miller et al. (1988) *Proc. Natl. Acad. Sci.* 85:856; Wang et al. (1990) *J. Bacteriol.* 172:949 for Campylobacter; and Cohen et al. (1973) *Proc. Natl. Acad. Sci.* 69:2110; Dower et al. (1988) *Nucleic Acids Res.* 16:6127; Kushner (1978) "An improved method for transformation of *Escherichia coli* with ColE1-derived plasmids" in *Genetic Engineering: Proceedings of the International Symposium on Genetic Engineering* (eds. H. W. Boyer and S. Nicosia); Mandel et al. (1970) *J. Mol. Biol.* 53:159; Taketo (1988) *Biochim. Biophys. Acta* 949:318, for Escherichia; and Chassy et al. (1987) *FEMS Microbiol. Lett.* 44:173, for Lactobacillus; and Fiedler et al. (1988) *Anal. Biochem* 170:38, for Pseudomonas; Augustin et al. (1990) *FEMS Microbiol. Lett.* 66:203, for Staphylococcus; and Barany et al. (1980) *J. Bacteriol.* 144:698; Harlander (1987) "Transformation of *Streptococcus lactis* by electroporation," in *Streptococcal Genetics* (ed. J. Ferretti and R. Curtiss III); Perry et al. (1981) *Infec. Immun.* 32:1295; Powell et al. (1988) *Appl. Environ. Microbiol.* 54:655; Somkuti et al. (1987) *Proc. 4th Evr. Cong. Biotechnology* 1:412, for Streptococcus.

The preferred bacterial host cell and expression vector are deposited at the American Type Culture Collection in Rockville, Md., under ATCC no. 39517.

After a host cell is constructed, it is cultured under conditions effective to induce production of hydrophobic polypeptides. Such culture conditions include those that permit transcription and translation of the coding sequence to produce the desired hydrophobic polypeptide. During induction of polypeptide production, the cells may be in either lag, exponential growth, or stationary phase. Thus, the cells need not be rapidly dividing during the induction of polypeptide production. Conditions that can affect bacterial production include, for example, aeration, pH, temperature, and medium composition. Examples of media components which affect production include, for example, carbon sources, such as glycerol and glucose, trace elements, amino acids, cations, and anions.

The inventors herein have discovered certain conditions that dramatically increase the expression of hydrophobic polypeptides, such as IFN-β polypeptides, in transformed host cells. Such conditions include the concentration of potassium or sodium cations in the medium, the pH of the medium, and the choice of carbon source.

For the claimed invention, the potassium cation concentration is "low". The potassium cation concentration of the present invention of the culture medium is no greater than about 120 mM; preferably, no greater than about 75 mM; more preferably, no greater than about 40 mM. To practice the present invention, no potassium need be added, however, in a preferred embodiment, the concentration of potassium is no less than about 10 mM; more preferably, no less than about 30 mM. Potassium cations can be added to the culture medium discontinuously in batches or continuously to provide a continuous, low concentration of potassium ions or potassium salts. For convenience, the following concentrations are recommended to be added as a bolus at the beginning of the culturing.

In another embodiment of the present invention, the sodium cation concentration is "very low". Usually, the sodium cation concentration herein is no greater than 40 mM; more usually, no greater than 5 mM; even more usually, no greater than 50 $\mu$M. Preferably, as much as possible, no sodium cations are intentionally added to culture medium. Sodium cations can be present in the medium, however, in the form of a contaminant from the vessel or from other components added. The concentration of contaminating sodium is typically less than about 10 mM; more typically, less than about 5 mM; even more typically, less than about 100 $\mu$M. Preferably, non-sodium containing trace elements, phosphate salts, acids, and bases are used in the medium to limit the amount of sodium cations as much as possible. For example, ammonium hydroxide is preferable used herein in place of sodium hydroxide.

When calculating the $K^+$ and $Na^+$ concentration in the present invention, the $Na^+$ and $K^+$ cations from the other components of the medium, such as, trace elements, phosphate salts, pH titrants, etc., are taken in account. Because the concentrations of $K^+$ and $Na^+$ preferred are so low, a pH titrant such as $NH_4OH$ is preferred, to avoid adding $K^+$ and $Na^+$ cations.

An effective energy source must be provided to the cells during culturing and production of hydrophobic polypeptides. Preferably, the energy source will not limit either the culturing time or final cell density or IFN-β polypeptide production. The effective energy source can include a single or a mixture of compounds. As discussed below, glycerol and glucose are preferred energy sources. Other compounds, such fructose, maltose, etc., may also be effective.

Glycerol is the preferred effective energy source. Applicants have found when glycerol is utilized, the growth rate and the polypeptide production rate is increased. In one embodiment, the cells are fed only glycerol. Glycerol, however, need not be the only energy source present. Energy sources that can be metabolized concurrently with glycerol may be present if they do not limit cell growth, culture time, or polypeptide production. For example, a small amount of glucose can be included in the culture medium with glycerol to reduce the lag phase of the cells. However, if production is linked to the tryptophan promoter, in a preferred embodiment of the present invention, then preferential metabolization of glycerol should begin just prior or at the time of tryptophan depletion. The amount of glucose, if any, should be limited under the circumstances.

Typically, when glycerol is the carbon source, the concentration will be at least about 20 g/L, more typically, the glycerol concentration will be between about 20 g/L and about 100 g/L. (The term "liter" is abbreviated interchangeably herein as "L" or "l"). Preferably, glycerol is available throughout the induction time. Usually, the concentration of other energy sources, e.g., glucose, will be less than about 10 g/L; more usually, less than about 5 g/L; even more usually less than about 2.5 g/L.

The amount of glycerol added to the cells is not critical as long as the amount of glycerol does not limit the final cell density. Typically, a sufficient amount of glycerol will be at least 1 g/L. E. coli cells can tolerate glycerol concentrations up to 100 g/L. The energy source can be supplied continuously or in batches throughout the culture period. Alternatively, the energy source can be supplied in one bolus at the beginning of the culture. For convenience, the cells are supplied with glycerol throughout the culture period.

Another preferred effective energy source is glucose. In one embodiment, glucose is fed at a limited rate. This feed strategy is unlike glycerol feed. Glucose is feed at or slightly less than the rate at which the cells metabolize the carbon source. One way to determine the limited rate of glucose is to monitor the polypeptide production for cultures with several glucose feed rates.

Inventors have also found that increased levels of acetate not only limit cell growth rates, but also depress hydrophobic polypeptide production rates. Yee et al., *Biotech. Bioeng.* 41: 781–790 (1993) noted that acetate is produced when one or more of the following conditions exist:

(1) oxygen limitation, i.e., anaerobic fermentation;
(2) nutrient excess, especially carbon source (C-source), such that the specific growth rate exceeds the growth rate at which acetate is formed (strain and media dependent);
(3) high partial pressure of $CO_2$.

Acetate production can be lessened by limiting glucose fed throughout the fermentation. Also, it is recommended that the cells are aerated with an excess of oxygen during fermentation. If glycerol is utilized as the effective energy source which does not limit final cell density, oxygen is required for metabolization of the glycerol.

The inventors found that as the temperature during cell culture decreased, the protein production per cell increase. Thus, in the present invention, the cells are grown at a temperature no less than 34° C.; more usually, no less than 37° C.; even more usually, no less than 39° C. Typically, for the claimed invention, the cells are grown at a temperature no greater than 42° C.; even more typically, no greater than 40° C.

In addition, the inventors found that the pH of the culture medium during hydrophobic polypeptide production can affect cell growth. Consequently, in an embodiment of the present invention, Preferably, the pH during induction is at least 4.8; more preferably, the pH is at least 5.4; even more preferably, the pH is at least 5.7. Usually, the pH during induction will be no greater than 6.8; more usually, the pH will be no greater than 6.3; even more usually, no greater than 6.0.

Additional amino acids may not be necessary for culturing bacterial host cells. However, supplementing the culture with additional amino acids just prior and during induction of polypeptide production or during the terminal portion of the culture time may be useful. Supplementation of amino acids during culturing of bacterial cells to increase expression is described in U.S. Pat. No. 4,656,132 and 4,894,334. Also, feeding additional amino acids to the culture may be desired to limit incorporation of unwanted amino acids, such as nor-leucine. For example, nor-leucine incorporation can be restricted by feeding a limiting amount of leucine with an excess of isoleucine. Alternatively, threonine or valine can also be added to the culture medium to avoid norleucine incorporation. Other amino acids can also be supplemented to the medium so as not to limit the production of polypeptides.

Other fermentation conditions such as inoculation time and number of cells, will be chosen by convenience, and such factors are not critical to the claimed invention. Also other medium components for inducing polypeptide production can include trace elements, carbon sources, vitamins, etc. Trace elements include copper, iron, manganese, zinc, magnesium, etc. Other carbon sources include amino acids, and lipids. These other media components are an example of the factors that are not critical to the invention and can be chosen for ease and convenience. Although the following are not critical to practice the invention, Applicants recommend that citrate and succinate are maintained in low concentrations during fermentation. Preferably, citrate and citrate salt concentrations are below 5 mM.

Purification of Hydrophobic Polypeptides

I. Harvest

The cells can be harvested at any time after induction. Time-production studies can be performed to determine the time after induction when the cells have produced the most hydrophobic polypeptide. For example, IFN-β polypeptide producing cells can be harvested by (1) concentration of the cells, or (2) removal of unwanted media components before disrupting the cells. Specifically, the cells can be spun at 20,000 g at 4° C. for 20 minutes, the supernatant removed, and then the cells can be resuspended at a concentration 100–200 $OD_{680}$ per mL in 0.1M sodium phosphate, pH 7.4, 0.15M NaCl in PBS. Alternatively, the cells can be concentrated five fold by circulating cross flow filtration, by circulating the material under pressure through a Millipore spiral ultrafiltration cartridge, for instance.

Applicants have found that lowering the ionic strength of the media before disrupting the cells can improve the separation of unwanted nucleic acids and membrane components from refractile bodies comprising hydrophobic polypeptides. See Dorin et al., U.S. Pat. No. 5,248,769, herein incorporated by reference. For example, IFN-β polypeptide producing cells can be separated from the fermentation media by centrifugation and resuspension in a low ionic strength buffer. The cells can be resuspended deionized water which optionally includes 1–2 mM ethylenediaminetetraacetic acid (EDTA), to chelate any remaining metal ions. Also, unwanted media components can be removed and the ionic strength lowered by diafiltering the cells against 5–10 volumes of deionized water which optionally includes 1–2 mM EDTA. Other chelators can be used in place of EDTA, such as ethyleneglycol-bis-(β-aminoethyl ether)-N,N,N',N'-tetraacetic acid (EGTA).

II. Primary Recovery

The first step of primary recovery is disrupting and optionally killing the cells producing hydrophobic polypeptide. After disrupting the cells producing IFN-β polypeptide, the isolated IFN-β polypeptide can be subjected to further processing, such as solubilization and denaturation procedures, or can be subjected to further purification of whole IFN-β refractile bodies, such as isolation by sucrose density centrifugation.

For example, the cells producing IFN-β polypeptide can be disrupted by utilizing beads, high pressure homogenization or sonication. Examples of disruption include homogenization at 6000–7000 psig, by either recycle mode or discrete pass mode (Preferably 3 passes at ~10°–15° C.). Alternatively, the cells can be disrupted by adding 0.2 μm beads as specified by Dynomill, mixing the beads and cells to disrupt the cells. Also, the cells can be disrupted by sonication using, e.g., a Heat Systems Model W-375 at maximum power for five minutes.

Next, to comply with regulation guidelines, the remaining undisrupted cells are killed. The cells may be killed using phenol, toluene, or octanol, for example. The addition of these reagents to the disrupted cells can cause physical changes to of the refractile bodies, such as density or hydrophobicity. These changes may be critical in the downstream processing purification of the desired hydrophobic polypeptides, such as IFN-β. Thus, the concentration of these reagents and the incubation time of these reagents with the disrupted cells can control the changes made to the refractile bodies. For example, disrupted cells that have produced IFN-β polypeptides can be incubated and agitated overnight with 1% (v/w) octanol at 0° C.–6° C. to inactivate the residual cells. Alternatively, the disrupted cells can be incubated with 0.25% (v/w) phenol and 0.25% (v/w) toluene for at least 30 minutes at about 37° C.

To improve the separation of cellular debris from refractile bodies, the ionic strength of the medium containing the disrupted cells can be lowered or the medium can be de-salted. Such techniques and procedures for lowering the ionic strength of the medium before redisrupting the disrupted cells are described in U.S. Pat. No. 4,748,234, herein incorporated by reference. For example, the disrupted cells that have produced IFN-β polypeptide can be centrifuged at 20,000 g for 20 minutes at 4° C., and the pellet resuspended in deionized water which optionally includes 1–2 mM EDTA, to chelate the remaining ions. Alternatively, EGTA can be added to between 1–2 mM to chelate the metal ions. Also, this mixture can be diafiltered against 5–10 volumes of deionized water with 1–2 mM EDTA.

Cellular debris can be dissociated from the refractile bodies by dispersing any aggregated material in the lysate by homogenization techniques. Homogenization techniques include sonication, mechanical agitation, or homogenization through a small aperture. For example, disrupted cells that produced IFN-β polypeptides can be dispersed again by sonication with a Heat Systems Model W-375 at maximum power for five minutes. Alternatively, the disruptate can be redispersed again passing it through a high pressure homogenizer three times at 6000–7000 psig.

The polypeptide refractile bodies can be further separated from the unwanted cellular components utilizing size or density differential methods. Low speed centrifugation is one method of separation. See Builder et al., U.S. Pat. No. 4,511,502, herein incorporated by reference. For example, IFN-β polypeptide refractile bodies can be sedimented using sucrose density centrifugation to separate them from unwanted cellular material. Factors which determine the effectiveness of the sucrose density centrifugation include the concentration of sucrose, the centrifugal force, and the residence time, or flow rate. The final concentration of the sucrose is critical. Using 1-octanol may limit the percentage of IFN-β polypeptide refractile bodies which will sediment. Preferably, sucrose is added to a final density between 1.0 and 1.18 g/mL. For example, sucrose is added to the disruptate to a final density of 1.08±0.01 g/mL.

To sediment the refractile bodies, either a continuous flow or lab centrifuge can be used. If a lab centrifuge is used, the IFN-β polypeptide refractile bodies, for example, are preferably spun at 8,000 g for at least 10 minutes. If a continuous flow centrifuge is used the centrifugal force, flow rate, and type of centrifuge are critical. For example, preferably, the mixture is centrifuged at 7,000 g at a flow rate of 0.25 L/minute in a Westfalia KA2 centrifuge or in a Sharples AS16 centrifuge at 15,500 g at a flow rate of 2–3 L/min. The sedimented material, called particle paste, is collected. If these centrifuges are used, they must be stopped to collect the refractile bodies from the centrifuge bowl. With a continuous flow centrifuge, the supernatant is continuously discharged. Other types of lab or continuous centrifuges may be utilized, and it is recognized that those skilled in the art can make the needed adjustments to centrifugal force and flow rate, for example, with these different centrifuges to produce an effective homogeneous sucrose cushion.

Hydrophobic polypeptides can be isolated effectively utilizing organic phase extraction. For example, IFN-β polypeptides can be effectively isolated from contaminants by organic extraction with a aliphatic alcohol. Such extraction methods are described in Konrad et al., U.S. Pat. No. 4,450,103; and Hanisch et al., U.S. Pat. No. 4,462,940; herein incorporated by reference. Most importantly, this type of extraction is effective at removing unwanted endotoxins. The extraction for IFN-β polypeptides is more effective if the IFN-β polypeptides are solubilized with a strong anionic detergent before extraction and if the detergent is present during extraction. The strong anionic surfactant apparently increases partition efficiency during organic extraction by reducing the cross-linking of contaminating proteins to the desired hydrophobic polypeptides.

Strong natural or synthetic anionic surfactants, such as alkali metal salts of fatty acids and alkali metal alkyl sulfates, are preferred for solubilization before organic extraction. Such agent will usually contain 10 to 14 carbon atoms. Sodium dodecyl sulfate (SDS) and sodium laurate are particularly preferred solubilizing agents. Examples of other solubilizing agents that can be used in the process include but are not limited to sodium dodecyl sulfonate, sodium dodecyl sulfate, sodium tetradecyl sulfate, sodium tridecyl sulfonate, sodium myristate, sodium caproylate, sodium dodecyl N-sarcosinate, and sodium tetradecyl N-sarcosinate.

The amount of solubilizing agent used in the solubilization depends upon the particular agent and the amount of protein to be solubilized. Typically, sufficient solubilizing agent to protein weight ratios range from about 1:1 to 10:1. When SDS is used, a SDS to protein ratio of about 1:1 to 10:1, preferably about 7:1 to 2.5:1, is used. Temperatures in the range of 15° C. to 60° C., are normally used in the solubilization. The solubilization is considered complete when the solution is substantially clear. For example, when the $OD_{280}$ of the solution reaches about 4.0 to 8.0, the solubilization process is considered complete.

For complete solubilization of the refractile bodies, the addition of a reducing agent is recommended. Dithiothreitol, β-mercaptoethanol, and thioglycolic acid are examples of reducing agents. For refractile bodies comprising IFN-β polypeptides the above reducing agents preferably are utilized at about 50 mM. Extremes in pH and/or temperature can facilitate or cause solubilization of IFN-β polypeptides as an example, adjusting the pH to between 9.0 to 11.0 in the solubilization buffer. Heating the mixture to 50° C. to 55° C. or as high as 95° C. for at least twenty minutes will facilitate solubilization. The time of solubilization will be lengthy if the refractile bodies are too concentrated. For IFN-β polypeptide refractile bodies, the protein concentration can range between 3–8 mg/mL, and the solubilization will proceed efficiently. However, solubilization and reduction of refractile bodies is efficient at protein concentrations of 0.5 to 25 mg/mL.

A chelating agent, such as EDTA, EGTA, or citrate, can be included in the solubilization buffer to scavenge unwanted metal ions, which may cause unwanted oxidation and reaggregation. For IFN-β polypeptides, typical hydrophobic polypeptides, the following concentrations are recommended, 2 mM EDTA, 2 mM EGTA, or 5 mM citrate.

Following the solubilization the ionic strength of the solution is adjusted, if necessary, to a level at which the solution and organic extractant will be substantially immiscible. The ionic strength will be in the range of 0.05 to 0.15. Inorganic salts, such as NaCl, may be added to the solution for this purpose. Such ionic strengths enable phase separation after the extraction. The extractants used in the process are 2-butanol, 2-methylbutanol, or mixtures, thereof. The mixtures preferably contain less than about 50% by volume 2-methylbutanol. 2-butanol is a preferred extractant for IFN-β polypeptides. Homologous alcohols were found to be ineffective extractants. The extractant will normally combined with the aqueous solution of IFN-β polypeptide in volumetric ratios in the range of about 0.8:1 to about 3:1, preferably about 1:1 (extractant:aqueous solution). The extraction may be carried out using conventional batch or continuous liquid-liquid extraction techniques and equipment. The extraction will normally be carried out at 20° C. to about 100° C. The extraction will involve contact times in the range of about one minute to one hour. The optimum contact time will depend upon the particular solubilizing agent:extractant combination. When SDS is used, shorter times in the above range may be used. When sodium laurate is used, longer times in the range are expected. The pH of the extraction mixture will range between about 6 and 9, with a pH of about 7.5 being preferred when SDS is used, and a pH of about 8.5 when sodium laurate is used.

Upon completion of the extraction the aqueous phase and extractant phase are separated, and the hydrophobic polypeptide is isolated from the extractant phase. The particular isolation procedure to be used will depend upon the solubilizing agent involved and the desired degree of purity. Various isolation techniques such as precipitation, molecular sieve chromatography, affinity chromatography, and electrophoresis may be employed.

When SDS is utilized with IFN-β polypeptide, other proteins can be precipitated from the extractant mixed with aqueous buffer at volumetric rations of about 2:1 to about 5:1, preferably about 3:1, by reducing the pH, typically to between 5 to 7, more typically about 6.5. The organic extract containing IFN-β polypeptide can be mixed with a buffer containing 0.1% SDS, in 10 mM phosphate, 0.9% saline, pH 7.4 and DTT is added to a final concentration of 5 mM to ensure that the IFN-β polypeptide remains in a reduced monomeric state. The mixture is allowed to come to about 20° C. Next, the pH organic extract can be adjusted to about 6.2±0.1 to precipitate the IFN-β polypeptides. The precipitate can be collected by centrifugation or filtration. For example, the precipitate isolated by centrifuging the mixture at with a Sharples AS16 centrifuge at 15,500 g at a flow rate of 2–3 liters/minute.

The precipitate can be resuspended in a buffer solution that is convenient for further purification procedures or refolding reactions.

III. Refolding—Oxidation

Refolding and oxidation conditions will vary from polypeptide to polypeptide. Typically, the polypeptide will be solubilized and reduced to monomer form before oxidation and refolding. The following are specific conditions for refolding IFN-β polypeptides.

IFN-β polypeptide resulting from the solubilizing of IFN-β refractile bodies can be refolded and oxidized into biologically active conformation under a range of conditions as shown in Mark et al., U.S. Pat. No. 4,518,584, herein incorporated by reference.

For refolding and oxidation conditions, two large scale manufacturing major concerns are kept in mind. First, maximizing throughput; and second, minimizing the resources utilized. An efficient bench scale process may not be cost effective when scaled up linearly. Thus, the process steps of the this invention may vary depending on the equipment and material that are available and cost effective. For example, IFN-β polypeptide may be refolded at a concentration as high as 1 mg/mL. This concentration may be preferred when the reaction vessel volume and buffer material are limited. However, the IFN-β polypeptide can be refolded at a concentration as low as 0.01 mg/mL. The concentration of IFN-β for refolding is also dependent on the amount of contaminant present. The higher the concentration of contaminating material the lower the concentration of IFN-β polypeptide is required for efficient refolding. For example, for a purity of approximately 90%, the optimal refolding concentration of IFN-β polypeptide is 0.13 mg/mL.

IFN-β polypeptide can be easily refolded without an additional oxidation reagent by removing the reducing agent (s), if one is present, and allowing oxidation with atmospheric oxygen. As shown in Example 8 of Mark et al., U.S. Pat. No. 4,518,584.

If desired, there are many known oxidation reagents that may be utilized to refold IFN-β polypeptides, for example, 8 $\mu$M CuCl$_2$ or 20 $\mu$M iodosobenzoic acid (IBA). In addition to the oxidation reagent, the oxidation buffer may contain a chelator, such as 1 mM EDTA or 1 mM EGTA, to prevent unwanted oxidation by metal ion contaminants. Obviously, chelators are not desired when copper ions are the oxidation reagent. A chaotropic agent can also be included in the oxidation buffer to reduce the amount of IFN-β polypeptide oligomers that are produced by the oxidation reaction. The chaotropic agent should not be such a high concentration that it prevents refolding altogether. Useful chaotropic agents include 0.1% SDS, 2M urea, and 2M guanidine hydrochloride. In addition, Applicants recommend that the pH during refolding and oxidation is maintained between 5.0 and 9.0.

One refolding/oxidation protocol is described in Mark et al., U.S. Pat. No. 4,518,584, Example 11. The IFN-β polypeptide was added in equimolar amounts to iodosobenzoic acid (IBA) into a reaction vessel containing 2 mM sodium pyrophosphate, 0.1% SDS and 1 mM EDTA. The pH was controlled during oxidation at 9.0±0.1 with 0.5N NaOH and adjusted to 5.5±0.2 when oxidation was complete. Alternatively, IFN-β polypeptide can be added in equimolar amounts to 15 $\mu$m IBA, 2 mM pyrophosphate, 0.1% SDS, and 1 mM EDTA buffer over 5 hours. The pH is maintained at 9.0±0.1 with NaOH. Next, iodosobenzoic acid is added to a 20 $\mu$M excess for an additional hour. The reaction can be terminated after about 7 to 7.5 hours by lowering the pH to between 5.2 and 5.7. The IFN-β polypeptide can undergo multiple oxidation reactions to increase the amount of refolded IFN-β polypeptide.

V. Column Chromatography

Column chromatography is one means herein of isolating hydrophobic polypeptides to the desired purity. Polypeptides can be isolated based on size, hydrophobicity, and other characteristics. The specific procedure is not critical and is chosen based on convenience. Examples of column chromatography procedures used to isolate IFN-β polypeptides, a typical hydrophobic polypeptide, are described in Mark et al., U.S. Pat. No. 4,518,584, and Lin et al., *Meth. Enzym.* 119: 183–192 (1986).

IFN-β polypeptides can be isolated based on charge, size or hydrophobicity characteristics. Specific examples of useful columns are high pressure liquid chromatography (HPLC), reverse phase HPLC, and SEPHACRYL® chromatography media. Several column runs or column types may be needed to remove the contaminants. The number or type of columns will be chosen according to the desired purification, timing, and financial parameters. The specific procedure chosen is not critical to the practice of the invention. Further, column chromatography may take place before or after refolding of the IFN-β polypeptide. Column chromatography is beneficial before refolding to remove contaminants which may interfere or limit IFN-β polypeptide refolding efficiency.

One column chromatography procedure utilizes two columns. The IFN-β polypeptides are chromatographed on a column loaded with SEPHACRYL® S-200 ion exchange gel filtration medium and then on a column loaded with SEPHADEX® G-75 gel filtration medium for a final purification to attain 99% purity. SEPHACRYL® and SEPHADEX® are registered trademarks of Pharmacia Fine Chemicals, Inc. SEPHACRYL® S-200 chromatography medium is a gel filtration liquid chromatography medium which is prepared from a covalently linked allyl dextran and N,N'-methylenebisacrylamide and has an exclusion limit of 250,000. SEPHADEX® G-75 medium is a bead-formed cross-linked dextran gel filtration medium First, solubilized IFN-β polypeptide refractile bodies were extracted with an organic solvent and acid precipitated. Next, the IFN-β polypeptides are chromatographed on dual 2.6×80 cm columns packed with SEPHACRYL® S-200 Superfine. Columns are equilibrated and eluted with 50 mM sodium acetate, 2 mM DTT, and 0.5 mM EDTA, pH 5.5. Sample volumes of 10–20 mM (5–10 mg protein/mL) and flow rates of 1–2 ml/minutes are recommended. Protein elution can be monitored by absorbance at 280 nm and biological activity can be quantitated by interferon assay (CPE).

Fractions of maximum IFN-β polypeptide purity and IFN-β biological activity are pooled. Purity can be assessed by SDS-PAGE and Coomassie stain. At this stage samples of interferon of greater than 95% purity are obtained. For many biological and chemical analyses, this level of purity is adequate. If material of greater than 99% purity is required, further gel permeation chromatography (SEPHADEX® G-75) is performed.

The major contaminants after SEPHACRYL® S-200 chromatography (low-molecular weight species which appear to be a mixture of IFN-β polypeptide fragments and *E. coli* proteins) are efficiently removed by additional gel filtration on SEPHADEX® G-75 (Superfine). After SEPHACRYL® S-200 chromatography the IFN-β polypeptide pool is concentrated and loaded onto a 2.6×80 cm column of SEPHADEX® G-75. The column was previously equilibrated with 50 mM sodium acetate, pH 5.5, 2 mM DTT, and 0.5 mM EDTA. This buffer is also used for protein elution. Sample volumes of 5–15 mL and flow rates of 0.5–1.0 mL/min are recommended. Effluent is again monitored by UV absorbance at 280 nm and fractions are evaluated by SDS-PAGE analysis and CPE assay.

Another IFN-β polypeptide column chromatography procedure utilizes three columns, SEPHACRYL® S-200 column run before and after refolding and a final SEPHADEX® G-75 to attain the desired level of purity.

Prior to chromatographic isolation, the solubilized IFN-β polypeptide refractile bodies are extracted by organic solvent and acid precipitated. The IFN-β polypeptide precipitate is resolubilized and treated with a reducing agent, such 20 mM DTT or 10 mM β-mercaptoethanol, to maintain the IFN-β polypeptide in the reduced, monomeric state. In addition, the IFN-β polypeptide precipitate can be resuspended with a chaotropic agent, such as 5% SDS or 6M urea, to monomeric IFN-β polypeptides. Also, to prevent formation of unwanted IFN-β polypeptide oligomers, chelators, such as 5 mM EDTA or 5 mM EGTA, can be added to scavenge metal ions which can promote oxidation of sulfhydryl groups. Useful buffers include 50 mM sodium phosphate or 50 mM Tris-HCl.

The pH is adjusted to 8.5±0.1 with sodium hydroxide and the solution is heated to between 45° C. to 55° C. for about 10 minutes, to facilitate reduction. The mixture is cooled to below 30° C. and the pH is adjusted to between 5.2 to 5.8 with glacial acetic acid and filtered through a 0.2 μm SARTOBRAN capsule filter.

SEPHACRYL® S-200 Superfine is a gel filtration liquid chromatography medium which is prepared from covalently linked allyl dextran and N,N'-methylenebisacrylamide with an exclusion limit of 250,000. The SEPHACRYL® S-200 medium is packed into six section Pharmacia stacked columns. The column is first equilibrated with NLT 80 L of 50 mM acetate buffer, 1% SDS, 1 mM EDTA, pH 5.5. The column is loaded with solubilized IFN-β polypeptide extracted with organic solvent and acid precipitated. The IFN-β polypeptide is eluted from the column with 50 mM acetate, 1% SDS, 1 mM EDTA, pH 5.5. After the IFN-β polypeptide is refolded, it is loaded and eluted from a Sephacryl® S-200 column according to the conditions described above. The desired fractions are pooled and concentrated to less than 4 liters using an Amicon ultrafiltration cartridge.

Sephadex® G-75 is a bead-formed, crosslinked dextran gel filtration medium. The column is equilibrated with NLT 80 L of 50 mM acetate buffer, 0.1% SDS, 1 mM EDTA, pH 5.5. The column is loaded with not more than 8 g of protein and the IFN-β polypeptide is eluted with the equilibration buffer. The pooled fractions containing IFN-β polypeptide may be held at 2°–8° C. for up to 6 months or at −20° C. or colder for one year prior to formulation.

V. Formulation

Formulation of the desired hydrophobic polypeptides will vary depending upon the specific polypeptide. Polypeptides can be formulated to stored in liquid, frozen, or lyophilized forms. The formulation can be chosen based on convenience. The following can be used to formulate IFN-β polypeptides for lyophilization.

The purified IFN-β polypeptide is formulated by adding the appropriate sterile components to protect the IFN-β polypeptide during all stages of storage and use.

The IFN-β polypeptides obtained in accordance with this invention may be formulated either as a single product or mixtures of the various IFN-β polypeptides. The IFN-β polypeptides are formulated with pharmaceutically acceptable preparations a physiologically compatible carrier media for clinical and therapeutic uses. Other physiologically compatible compounds may also be included in the formulation, such as dextrose, human serum albumin, etc.

The IFN-β formulation can contain a concentration IFN-β polypeptide between 0.25 mg/mL to 15 mg/ml. The amount of IFN-β polypeptide included in the formulation is not critical to the invention and will depend on the dosage to given for a particular indication and delivery regimen.

Sugars can be utilized in formulating IFN-β polypeptides include mannitol, dextrose, and sucrose. Typically, for a formulation to be lyophilized, the concentration of mannitol is between 1% (wt/v) and 5% (wt/v); more typically, the concentration is approximately 2.5%. For dextrose, the concentration is between 0.5% (wt/v) and 2% (wt/v); more usually, the concentration is approximately 1.25% (wt/v). For IFN-β polypeptide formulation, the sucrose concentration is between 1% (wt/v) and 5% (wt/v); more usually, the concentration is approximately 1.75%.

Examples of amorphous protectants that can be included in IFN-β polypeptide formulations are dextran, trehalose, 2-hydroxypropyl-β-cyclodextrin, amino acids, such as glycine, or human serum albumin. These protectants help reduce the physical and chemical alterations to the IFN-β polypeptides, such as oxidation, etc. An effective amount of amorphous protectant will prevent unwanted aggregation, chemical linkage, oxidation and degradation of IFN-β polypeptide. Too much amorphous protectant will hinder efficient lyophilization, and too little will reduce the shelf life of lyophilized product.

Glycine can be added to the IFN-β polypeptide formulation to a final concentration of at least 0.01% (wt/v), more usually at least 0.3% (wt/v). Preferably, the glycine concentration in the formulation is no more than 1% (wt/v), more preferably no more than 0.7% (wt/v).

Human serum albumin (HSA) can also be added to the formulation as a protectant. Typically, HSA is added to the IFN-β polypeptide formulation to a final concentration of at least 0.01% (wt/v), more usually at least 0.5% (wt/v). Preferably, the glycine concentration in the formulation is no more than 2.5% (wt/v), more preferably no more than 1.25% (wt/v).

Buffers can be utilized to maintain the pH of the formulation during lyophilization, storage, and once the IFN-β polypeptide is reconstituted. Maintenance of pH is critical to prevent such physical and chemical alterations, such as oxidation, during storage of the IFN-β polypeptide. The pH will be chosen not only to optimize the longevity of the IFN-β polypeptide but to ease administration of the IFN-β polypeptide to humans. Usually, the pH of the formulation is adjusted to between 6.0 and 7.5 with NaOH if a sodium containing buffering reagent is used. More preferably the pH is adjusted to 6.5.

Sodium citrate or phosphate are examples of amorphous buffers. Sodium citrate, is added to the formulation to a final concentration of at least 1 mM, and more preferably at least 4 mM. Typically, the concentration of sodium citrate in the formulation is no more than 10 mM, and more typically no more than 6 mM.

Once the IFN-β polypeptides are formulated as desired, such a formulation can be stored as a frozen liquid or lyophilized. The form for storage of an IFN-β polypeptide formulation is not critical for the instant invention and chosen for convenience.

U.S. Pat. No. 5,183,746 describes IFN-β liquid formulations that are stored as frozen liquids instead in the lyophilized form. According to the '746 patent, frozen liquid formulations can contain glycerol and a combination of biocompatible non-ionic polymeric detergents and a small amount of buffer to maintain the formulation at the desired pH.

Preferred concentrations of glycerol are from about 0.005% to about 5%; more preferably, from about 0.01% to about 3%; even more preferably from about 0.05% to about 1.5%. When glycerol is present in the liquid formulations at a concentration range by volume of from about 5% to about 50%, preferably from about 20% to about 30% and more preferably about 25%, the combination of non-ionic detergents acting with the glycerol can be added to a lower concentration, and the preferred concentration are from about 0.0005% to about 5%, preferably, from about 0.001% to about 1%, and more preferably, from about 0.01% to about 0.5%. A preferred detergent is SDS.

For example, the liquid formulation may lyophilized according to techniques known in the art. Typically, lyophilization procedure comprise a freezing step, a primary drying step, and a secondary drying step.

The formulation is frozen in order to:
(1) freeze the protein;
(2) freeze the unwanted water; and
(3) form a matrix, to facilitate reconstitution of the protein.

During the freezing step, the formulation may undergo several temperature shifts to freeze and to properly crystallize the formulation components. See Williams et al., *J. Parent. Sci. Tech.* 38(2): 48–59 (1984), at page 49, bottom right column. These shifts in temperature are performed at normal atmospheric pressures, and thus, the formulation is not being dried during these temperature shifts.

In order to freeze the water in the formulation, freezing temperature is below 0° C.; more typically, below −20° C.; even more typically, the formulation is frozen below −50° C. The vials containing the formulation can be frozen in the lyophilizer at atmospheric pressure. The temperature of the formulation is controlled by the shelf temperature in the lyophilizer. Typically, the vials are placed on a pre-cooled shelf, 10° C., for example, and then the shelf temperature is lowered to freeze the formulation. The temperature can be lowered at a rate of between 33° C. per hour and approximately, 45° C. per hour. The formulation should be held at the desired temperature for about 30 minutes to two hours or more.

Next, the formulation is dried in two steps, primary and secondary drying. During both steps, the chamber pressure is reduced below atmospheric pressures to force the water to proceed directly from solid to gas phase, i.e., sublimate. The primary drying begins after the formulation is frozen, and most of the water is removed by this step. During primary drying, the pressure in the sample chamber is reduced, and the shelf temperature of the lyophilizer is raised and held constant at a primary drying temperature. The shelf temperature is held constant to allow the product temperature to equilibrate with the shelf temperature as shown in FIG. 1 on page 49 of Williams et al., supra. The water vapor is discharged into the condenser of the lyophilizer, which re-freezes the vapor.

The pressure in the sample chamber is reduced to "subatmospheric pressures." Subatmospheric pressures refer to any pressure below one atmosphere unit. Preferably the subatmospheric pressure will between 500 and 10 μmHg; more preferably between 200 to 50 μm Hg; even more preferably about 70 μmHg.

Typically, the liquid formulation or frozen product temperature is adjusted by changing the shelf temperature of the lyophilizer. The sample temperature, whether the sample is solid or liquid, usually lags behind the shelf temperature. The sample temperature can be changed to a target temperature by two techniques. First, the shelf temperature may be changed and held constant at a target temperature until the sample equilibrates with the shelf temperature. Or the shelf temperature can be adjusted slowly to a target temperature so that the temperature difference between the shelf and the sample is minimal. Either method is effective for changing the sample temperature. The choice of techniques will depend on the desired rate of temperature change. However, the temperature should not be increased so quickly that the water evaporates instead of lyophilizes from the product.

Typically, the shelf temperature is raised to between about −20° C. and −5° C. for primary drying. The temperature is raised to the primary drying temperature at a rate of between about 30° C. per hour to about 60° C. per hour. The formulation is held at the desired primary drying temperature between about 3 to 15 hours.

After primary drying is completed, again under reduced chamber pressure, the shelf temperature is raised to a secondary drying temperature and then held constant. The shelf temperature is held constant to allow the product temperature to equilibrate with the shelf temperature. During secondary drying, water which is tightly bound to the product is removed.

Typically, the shelf temperature is raised to between about 15° C. and 30° C. for secondary drying. The temperature is raised to the secondary drying temperature at a rate of between about 30° C. per hour to about 60° C. per hour. The formulation is held at the desired primary drying temperature somewhere between about 3 to 15 hours.

The vials can be stoppered under pressure with a variety of gases. The chamber can be pressurized between 12 psi with the desired gas. Gases that limit the chemical modification of IFN-β polypeptides are preferred, such as $N_2$.

All patents, patent applications, and other publications cited are herein incorporated by reference.

C. Examples

The examples presented below are provided as a further guide to the practitioner of ordinary skill in the art, and are not to be construed as limiting the invention in any way.

Example 1: Construction of a Cell Capable of Producing IFN-β Polypeptide

An *Escherichia coli* host cell was transformed with an expression vector containing a gene encoding an IFN-β polypeptide. The encoded IFN-β polypeptide has the same sequence as SEQ ID NO:1 except it has a serine in place of a cysteine at position 17 of SEQ ID NO:1. The construction of this cell line is described in Mark et al., U.S. Pat. No. 4,518,584, herein incorporated by reference.

The human IFN-β gene was isolated, modified and transferred into a prokaryotic host, *E. coli,* creating a cell capable of IFN-β polypeptide production. The native IFN-β gene was modified to encode a protein which has a serine in place a cysteine at amino acid position 17, according to SEQ ID NO:1.

This modification was made to preclude the formation of IFN-β polypeptides with undesirable tertiary structure due to incorrect disulfide bonding between cysteine residues. The cysteine at residue position 17 does not participate in disulfide bonding in the active native human IFN-β polypeptide. Thus, site-directed mutagenesis was used to substitute a serine in place of the cysteine to prevent unwanted disulfide bonding.

To do this, first, the native human IFN-β gene was isolated and its leader peptide sequences deleted. The *E. coli* trp promoter sequence was isolated and vector incorporating these components was constructed. The IFN-β gene was subcloned into bacteriophage M13mp8 to produce a single stranded DNA containing the native human IFN-β coding sequence. The codon for the amino acid cysteine at position 17 was modified to encode a serine. The phage DNA containing the serine modified IFN-β polypeptide gene was isolated.

The modified gene was excised from the phage DNA and inserted into a vector containing a correctly oriented *E. coli* trp promoter. This vector was designated plasmid pSY2501. *E. coli* strain MM294-1 was transformed with this plasmid to create a cell capable of producing an IFN-β polypeptide.

Specifically, a clone, 4E1, was used containing the complete sequence encoding the native mature human IFN-β protein and its leader peptide. In order to remove the sequence for the leader peptide, the gene was isolated by digesting the clone with HhaI restriction enzyme and the 1.2 kilobase double stranded HhaI fragment containing the IFN-β sequence was melted to separate the DNA into single stranded cDNA. A synthetic oligonucleotide with the sequence TATGAGCTACAAC (SEQ ID NO:2) was used to hybridize to the DNA adjacent to the leader peptide sequence. The 5' end of the oligonucleotide began with the base T in order to regenerate a HindIII sight preceding the initiation codon ATG. DNA polymerase I treatment (3' to 5' exonucleolytic activity) removed the single stranded DNA coding for the leader peptide. The enzyme's polymerase activity then restored the native human IFN-β sequence to a double stranded cDNA with a 5' blunt ended terminus. PstI restriction enzyme was used to cleave the repaired DNA, resulting in a 144 base pair (bp) fragment encoding the N-terminus portion of the native human IFN-β gene. The IFN-β cDNA was now a 5' blunt ended fragment beginning with the base T, followed by the initiation codon ATG which codes for the mature protein's N-terminus methionine, and ending at the PstI site of the gene.

To obtain the full length native human IFN-β sequence, the fragment encoding the C-terminus of the native human IFN-β sequence was isolated from the original clone 4E1 by digesting it with PstI and BglII restriction enzymes and recovering the 359 bp PstI-BglII fragment. In preparation for insertion of the IFN-β cDNA, plasmid pBR322 was cleaved with HindIII restriction enzyme, followed by DNA polymerase I treatment to blunt-end the HindIII site. BamHI restriction enzyme was then used to remove a portion of the open plasmid as a repaired HindIII-BamHI fragment. The N-terminus and C-terminus encoding IFN-β fragments were then inserted into the prepared pBR322 in a three way ligation: the repaired 5' end of the IFN-β N-terminus fragment was blunt-ended ligated to the repaired HindIII site, the 3' PstI end of the N-terminus fragment and the 5' PstI end of the C-terminus encoding fragment were ligated, and the 3' BglII site of the C-terminus encoding fragment was ligated to the BamHI cohesive end in pBR322 to create an XhoII site. The resulting clone was designated pβ1-25.

Plasmid ptrp3 was the source for the trp promoter. The trp promoter was isolated from ptrp3 by cleaved with EcoRI and HindIII restriction enzymes. These enzymes were also used to cleave plasmid pβ1-25, removing the intervening EcoRI-HindIII sequence. The fragment containing the trp promoter was ligated into pβ1-25 as an EcoRI-HindIII fragment. The resulting clone, designated pβ1-trp.

For the site directed mutagenesis, restriction enzymes HindIII and XhoII were used to excise the native human IFN-β coding sequence from plasmid pβ1-trp. A short section of double stranded, Replicative Form (RF) M13mp8 phage DNA was removed by cleavage with restriction enzymes HindIII and BamHI to accommodate with the IFN-β sequence which was then ligated into place. Sites cleaved with XhoII and BamHI have compatible sticky ends; in this case the resultant ligation regenerated the XhoII site. The recombinant phage DNA was transformed into competent cells of E. coli strain JM103, which is a strain commonly used for the production of M13 phage DNA. Restriction enzymes were used to identify RF clones containing the IFN-β gene. One such clone, designated M13-β1 was used to prepare single stranded phage DNA to serve as the template for site specific mutagenesis.

The required mutation was accomplished by manufacturing a synthetic oligonucleotide primer whose sequence: GCAATTTTCAGAGTCAG (SEQ ID NO:3) is identical to a seventeen nucleotide sequence in the sense strand of IFN-β around the region of codon 17, except for a single base pair mismatch. This mismatch at nucleotide 12 of the primer substituted A for the native T, resulting in the substitution of serine for cysteine at amino acid position 17. The base substitution also created a new HinFI site, which facilitated detection of the serine-17 mutation.

Hybridization of the synthetic primer to the phage DNA was followed by primer extension, using DNA polymerase I Klenow fragment to form double stranded DNA (RF) which was used to transform competent cells of E. coli strain JM103. Transformed E. coli colonies extruded single stranded progeny phage whose DNA encoded either the mutated IFN-$β_{ser17}$ sequence, or the native human IFN-β polypeptide. Selection for phage progeny carrying the mutated IFN-β gene was carried out using a 32P-labeled form of the above synthetic primer as a probe. The probe was fully complementary to the DNA region containing the $Cys_{17}$ to $Ser_{17}$ mutation, and therefore hybridized most strongly to phage DNA carrying the mutation. One phage clone that hybridized to the probe was designated M13-SY2501; detection of the new HinfI restriction site in this clone also indicated the presence of the correct single base mutation. Dideoxy sequencing of the single stranded form of M13-SY2501 confirmed that the TGT Cys codon was converted to an AGT Ser codon.

The mutated IFN-β gene was excised from phage M13-SY2501 RF DNA by cleaved with HindIII and XhoII. Plasmid ptrp3 containing the E. coli trp promoter was cleaved with HindIII and BamHI, which removed a portion of DNA just 3' to the trp promoter. This inactivated the plasmid gene for tetracycline resistance. The IFN-$β_{ser17}$ fragment was then ligated into the HindIII and BamHI sites of ptrp3 with T4 DNA ligase, and the ligated DNA was transformed into E. coli strain MM294.

Plasmid pSY2501 was transformed into a competent subvariant of E. coli strain MM294 designated MM294-1 and expression of IFN-$β_{ser17}$ was verified. Samples of the transformed cells were deposited in the Cetus Master Culture Collection and the American Type Culture collection, Rockville, Md., under ATCC no. 39517.

As described, the IFN-$β_{ser17}$ gene is under the control of a trp promoter and is present within E. coli as a multicopy plasmid. Expression of the gene is determined by the intracellular level of tryptophan. Molecules of this amino acid form complexes with the intracellular trp repressor protein and this complex binds to the operator region of the trp promoter/operator, preventing IFN-$β_{ser17}$ gene transcription. Therefore, in the presence of an intracellular source of tryptophan, IFN-$β_{ser17}$ production is repressed. During culture growth, the extracellular tryptophan is consumed and its concentration drops. Because the rate of tryptophan consumption is proportional to the amount of cell growth, the cell density at which the tryptophan is fully consumed may be predicted. At this point, the promoter/operation region is freed from the trp repressor/tryptophan complex and the RNA polymerase is able to transcribe the IFN-$β_{ser17}$ gene. The cloned trp promoter includes a ribosome binding site sequence so that the transcribed IFN-$β_{ser17}$ mRNA is translated by E. coli ribosomes. Because the same trp promoter system also controls the expression of the proteins needed to biosynthesize tryptophan, the cells can maintain an adequate supply of tryptophan even without an extracellular source.

Plasmid ptrp3 was created by subcloning the E. coli trp promoter from plasmid pVV1 as a repaired (blunt-ended) HhaI-TaqI partial fragment of 100 bp. It was inserted into the repaired (blunt-ended) EcoRI-ClaI sites of pBR322, regenerating both the EcoRI and ClaI sites.

The strain used for production of IFN-$β_{ser17}$ is an E. coli K-12 strain known as MM294-1, which was originally derived from strain MM294. Meselson described MM294, also called 1100.293, and identified it as lacking an enzyme which destroys foreign DNA, a characteristic making the strain useful for transformation. The strain has no special nutritional requirement except thiamine, allowing it to grow rapidly on thiamine-supplemented minimal medium in fermentors.

The variant MM-294 was isolated from a IFN-β producing clone of MM294 which had been transformed with the IFN-β plasmid pSY201, and differs from MM294 in the level of expression of the IFN-β gene. The pSY2101 plasmid expressed IFN-β at higher levels in this culture than in other MM294 clones. It was necessary to remove the pSY2101 plasmid, which encoded the native human IFN-β polypeptide with $Cys_{17}$. The bacterium was cured of the pSY2101 plasmid by culturing under expressing conditions and replica plating, selecting for colonies which had lost antibiotic resistance. The isolate host was renamed MM294-1.

Cultures of pSY2501 and pβ1trp, which include progeny thereof, were grown up to an optical density ($OD_{600}$) of 1.0. Cell free extracts were prepared and the amount of IFN-β antiviral activity assayed on GM2767 cells in a microtiter assay. Extracts of clone pSY2501 exhibit three to ten times higher activity than pβ1trp (Table 1), indicating that clone pSY2501 was either synthesizing more protein exhibiting IFN-β activity or that the protein made had a higher specific activity.

The recovered product was assayed for native, human IFN-β activity using an assay based on viral protection. The procedure was performed in microtiter plates. First, 50 μL of minimum essential medium were charged into each well, and 25 μl of the sample was placed in the first well, and 1:3 volume dilutions were made serially into the following wells. Vesicular Stomatitis virus, human fibroblast cell line GM-2767, and reference IFN-β controls were included on each plate. The reference IFN-β used was 100 units per mL. The plates were then irradiated with UV light for 10 minutes. After irradiation 10 μl of the cell suspension ($1.2 \times 10^5$ cells/ml) were added to each well and the trays were incubated for 18–24 hours. A virus solution at one plaque-forming unit per cell was added to each well except the cell control. The trays were then incubated until the virus control showed 100% (CPE). This normally occurred 18–24 hours after adding the virus solution. Assay results were interpreted in relation to the location of the 50% CPE well of the reference IFN-β control. From this point the titer of interferon for all samples on the plate was determined.

The IFN-β polypeptide, with the ser17 substitution, was also compared in its antiviral activity to native, human IFN-β. Inhibition of vesicular stomatitis virus replication in diploid foreskin fibroblast (HS27F) was indistinguishable from that of the natural molecule. Similarly, inhibition of herpes simplex virus type 1 in HS27F fibroblasts by the natural and mutant proteins were comparable. This procedure and results were described in Mark et al., *Proc. Natl. Acad. Sci. USA* 81: 5662–5666 (1984).

The antiproliferation activity of IFN-β polypeptide, ser17 substitution, for continuous cell lines was compared with that of native, human IFN-β. T24 cells derived from a transitional cell carcinoma were treated with 200 units/ml of the proteins. Cell growth was inhibited significantly. (p>0.2) by both proteins. This procedure and results were described in Mark et al., *Proc. Natl. Acad. Sci. USA* 81: 5662–5666 (1984).

The ability of IFN-β polypeptide, ser17 substitution, to stimulate natural killer (NK) cell (spontaneous cell mediated cytotoxicity) activity was tested. The IFN-β polypeptide was tested with two cell types: (1) Ficoll-hypaque separated peripheral human mononuclear cells (PMC); or (2) NK-enriched lymphocyte preparations depleted of monocytes by plastic adherence and of OKT3-positive T cells by treatment with OKT3 antibody plus complement. The cells were incubated overnight in growth medium containing various concentrations of IFN-β polypeptide, ser17 substitution. $^{51}$CR-labeled target cells were incubated with the effector cells for 2–4 hours. The effector cell to target cell ratio was 50:1. NK cell cytoxicity was determined by measuring the amount of label released into the medium. This procedure and results were described in Mark et al., *Proc. Natl. Acad. Sci. USA* 81: 5662–5666 (1984).

Example 2: Control Experiment

This experiment relates to fermentation of a cell capable of producing IFN-β polypeptide under conditions of high potassium and sodium cation concentrations, and glucose as the effective non-limiting energy source. Further, the cells were cultured at 37° C. and pH 6.8 with KOH as a titrant.

*E.coli,* strain MM294-1 cells transformed with pSY2501, described in Example 1, were cultured in the following medium:

| Compound | g/L |
|---|---|
| Water | 8 L |
| Potassium Phosphate (monobasic) | 2.94 |
| Ammonium Sulfate | 9.52 |
| Sodium Citrate | 0.441 |
| Magnesium Sulfate (heptahydrate) | 0.492 |
| Ferrous Sulfate (heptahydrate) | 0.0278 |
| Manganous Sulfate (monohydrate) | 0.00508 |
| Zinc Sulfate (heptahydrate) | 0.00864 |
| Cupric Sulfate (pentahydrate) | 0.00025 |
| Tryptophan | 0.07 |
| Thiamine | 0.02 |
| Glucose | 50.0 |

The cells were maintained at pH 6.8 throughout the fermentation using potassium hydroxide as a titrant. Further, the cells were cultured at 37° C. at 40% dissolved oxygen.

A typical fermentation run following these procedures produced an average of approximately 350 mg/L of IFN-β polypeptide. Further, an average of approximately 5% of the total cell protein was IFN-β polypeptide. IFN-β polypeptide concentration was determined by SDS-PAGE analysis with a IFN-β polypeptide standard. Total protein content was assayed using a standard Lowry protocol.

Example 3: Effect of Potassium Concentration on Cell Growth and IFN-β Polypeptide Production These fermentor experiments revealed that cell growth and production of cells capable of producing IFN-β polypeptide are limited by concentration of K$^+$ cations.

*E.coli,* strain MM294 cells transformed with pSY2501, described in Example 1, were cultured in the basal medium, below, with varying concentrations of potassium cations with a fixed concentration of sodium cations.

The cells were cultured in one of three media described below:

~40 mM Potassium Cation Medium 4.4 mM potassium citrate 26.8 mM KH$_2$PO$_4$ 66.8 mM (NH$_4$)$_2$SO$_4$ 33.2 mM NH$_4$H$_2$PO$_4$ 10 mM MgSO$_4$ 2 g/L glucose 20 g/L glycerol 140 mg/L tryptophan 24 mg/L thiamine 4.7 mL/L BTM (trace elements)

~75 mM Potassium Cation Medium 4.4 mM potassium citrate 35 mM KH$_2$PO$_4$ 72 mM (NH$_4$)$_2$SO$_4$ 5 mM MgSO$_4$ 2 g/L glucose 20 g/L glycerol 30 mM KCl 70 mg/L tryptophan 24 mg/L thiamine 50 mg/L ampicillin 4.7 mL/L BTM (trace elements)

5 mM MgSO$_4$ and 15 mM KH$_2$PO$_4$ were added at 40 OD$_{680}$.

~120 mM Potassium Cation Medium 4.4 mM potassium citrate 35 mM KH$_2$PO$_4$ 72 mM (NH$_4$)$_2$SO$_4$ 5 mM MgSO$_4$ 2 g/L glucose 20 g/L glycerol 60 mM KCl 70 mg/L tryptophan 24 mg/L thiamine 4.7 mL/L BTM (trace elements)

5 mM MgSO$_4$, 15 mM KH$_2$PO$_4$, and 40 mM (NH$_4$)$_2$SO$_4$ were added at 32 OD$_{680}$.

Ten mL of polypropylene glycol antifoam was added and the fermentor was inoculated with approximately 10 mg (dry weight) of cells.

The fermentation medium was maintained at a pH of 5.7 with 7.4N NH$_4$OH. Fifty percent (v/v) glycerol was fed at a 3.5:1 ratio with the ammonium hydroxide. The initial glycerol volume in the feed reservoir should be 150 mL/L of fermentor working volume. The temperature was maintained at 37° C. The cells were harvested seven hours after reaching an optical density of 16 OD$_{680}$ units.

Figure 2:
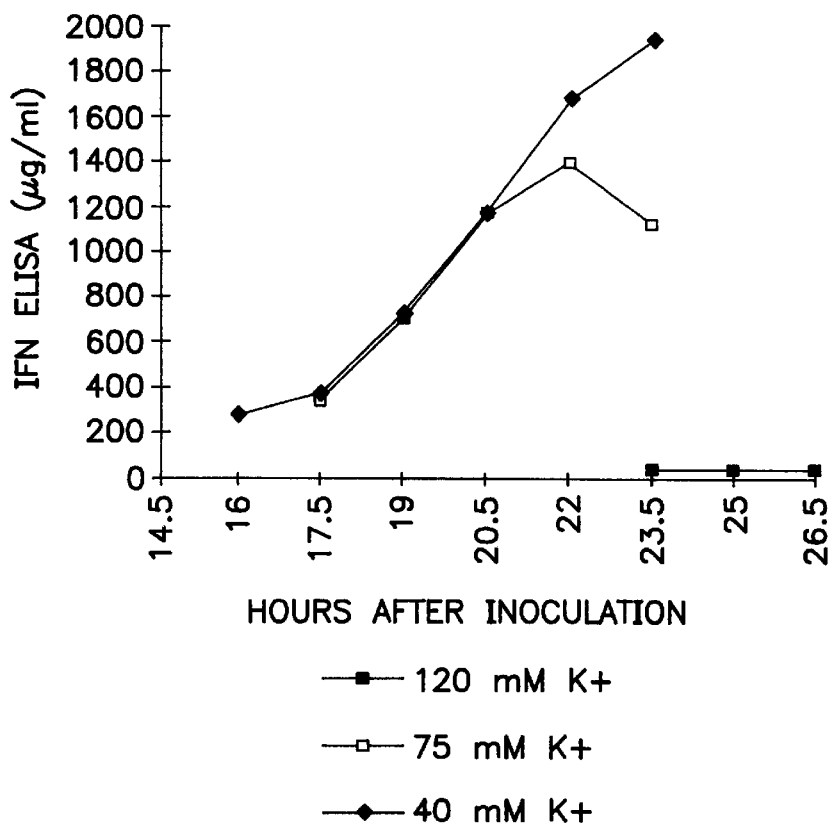
FIG. 2 demonstrates the effect of potassium concentration on polypeptide expression.

Each culture contained one of the following approximately concentrations of potassium cations: 40 mM, 75 mM, and 120 mM. The resulting growth rates and IFN-β polypeptide production rates of each culture are shown in FIGS. 1 and 2. At 23.5 hours, the 75 mM culture reached an optical density (OD$_{680}$) of approximately 85 units compared to approximately 35 units, more than a two fold difference, than the 120 mM culture.

Though the 75 mM culture grew to a higher cell density than the 40 mM culture, the 40 mM culture produced almost 2000 μg/mL of IFN-β polypeptide in contrast to the 75 mM culture which only produced somewhat less than 1200 μg/mL. The production of IFN-β polypeptide increased approximately 60% when 40 mM K$^+$ was used instead of 75 mM K$^+$. The 120 mM culture produced almost no IFN-β polypeptide.

The production levels of IFN-β polypeptide was measured by SDS-PAGE analysis stained with Coomassie.

Example 4: The Effects of Potassium and Sodium cations on Cell Growth and IFN-β Polypeptide Production The following shake flask experiments demonstrated that cells capable of producing IFN-β polypeptides are sensitive to the potassium and sodium cation concentration.

*E.coli*, strain MM294 cells transformed with pSY2501, described in Example 1, were cultured in the basal medium, below, with varying amounts of potassium and sodium cations added.

The following basal media was used for the potassium/sodium cation experiments:

4.4 mM ammonium citrate
40 mM (NH$_4$)$_2$SO$_4$
35 MM NH$_4$H$_2$PO$_4$
6 mM MgSO$_4$
5 g/L glycerol
24 mg/L thiamine
4.7 mL/L BTM* (trace elements)
50 mM MES buffer

*The components of BTM are as described in Example 2.

Sodium and potassium cations were added as KCl and NaCl to individual flasks to the desired concentration.

The cells were cultured in a fermentor until exponential growth phase in defined medium containing tryptophan. The cells were then inoculated at the desired cell density in the above basal media with the desired concentration of potassium and sodium cations. This media were added to sterilized shake flasks.

Figure 3:
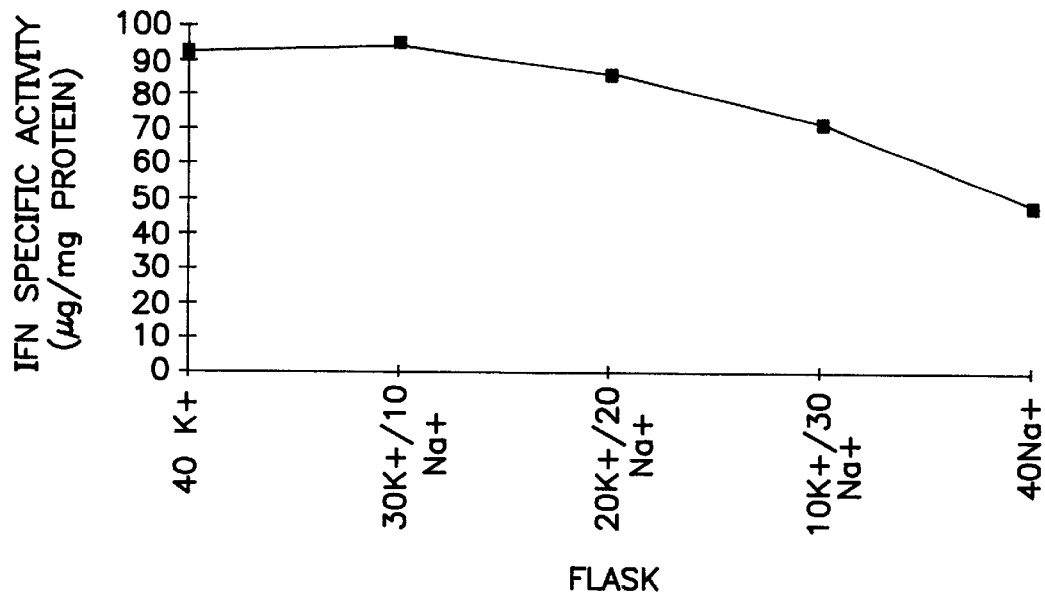
FIG. 3 depicts the effect of the $K^+/Na^+$ on expression of IFN-β polypeptide, an example of a hydrophobic polypeptide.

Each culture contained one of the following concentrations of potassium and sodium salts, 40 mM K$^+$/0 mM Na$^+$, 30 mM K$^+$/10 mM Na$^+$, 20 mM K$^+$/20 mM Na$^+$, 10 mM K$^+$/30 mM Na$^+$, 0 mM K$^+$/40 mM Na$^+$. The resulting IFN-β polypeptide production rate of each culture is shown in FIG. 3. The culture with no K$^+$ cations and 40 mM Na$^+$ produced approximately 50 μg of IFN-β polypeptide per mg of total cell protein. The culture with 40 mM K$^+$/0 mM Na$^+$ produced approximately 90 μg of IFN-β polypeptide per mg of total cell protein. This is approximately a 80% improvement in yield.

The IFN-β polypeptide concentration was measured by ELISA. The total protein concentration was assayed using a BCA assay, Pierce Chemical. Cell density was measured using Klett units.

Example 5: The Effect of pH on Cell Growth After Induction of IFN-β Polypeptide Production These shake flask experiments established that cell growth after induction of IFN-β production is limited by high pH.

*E.coli*, strain MM294-1 cells transformed with pSY2501, described in Example 1, were cultured in the basal medium, below, titrated to varying pH.

For these experiments, the following basal medium was used and adjusted to the desired pH with either NH$_4$OH or HCl:

12 mM NH$_4$Cl
26.3 mM KH$_2$PO$_4$
33.7 mM Na$_2$HPO$_4$
10.8 mM K$_2$SO$_4$
0.24 mM MgSO$_4$
5 g/L glycerol
3.6 μM ZnSO$_4$
3.6 μM MnSO$_4$
0.12 μM CuSO$_4$
50 mM MES buffer The cells were grown in a pre-induction medium containing tryptophan to exponential growth phase. During pre-induction the cultures were maintained at the various desired pH. The cells were then separated from the medium by centrifugation and then resuspended in the medium with the desired pH. The temperature was maintained at 37° C.

Figure 4:
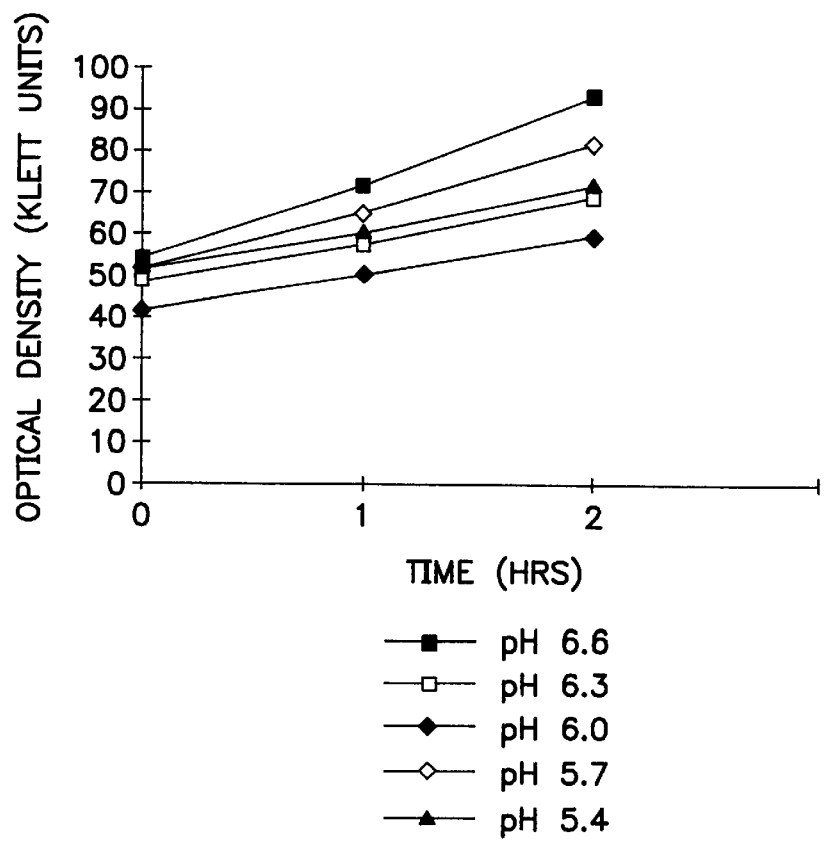
FIG. 4 depicts the effect of pH on cell growth before induction.
Figure 5:
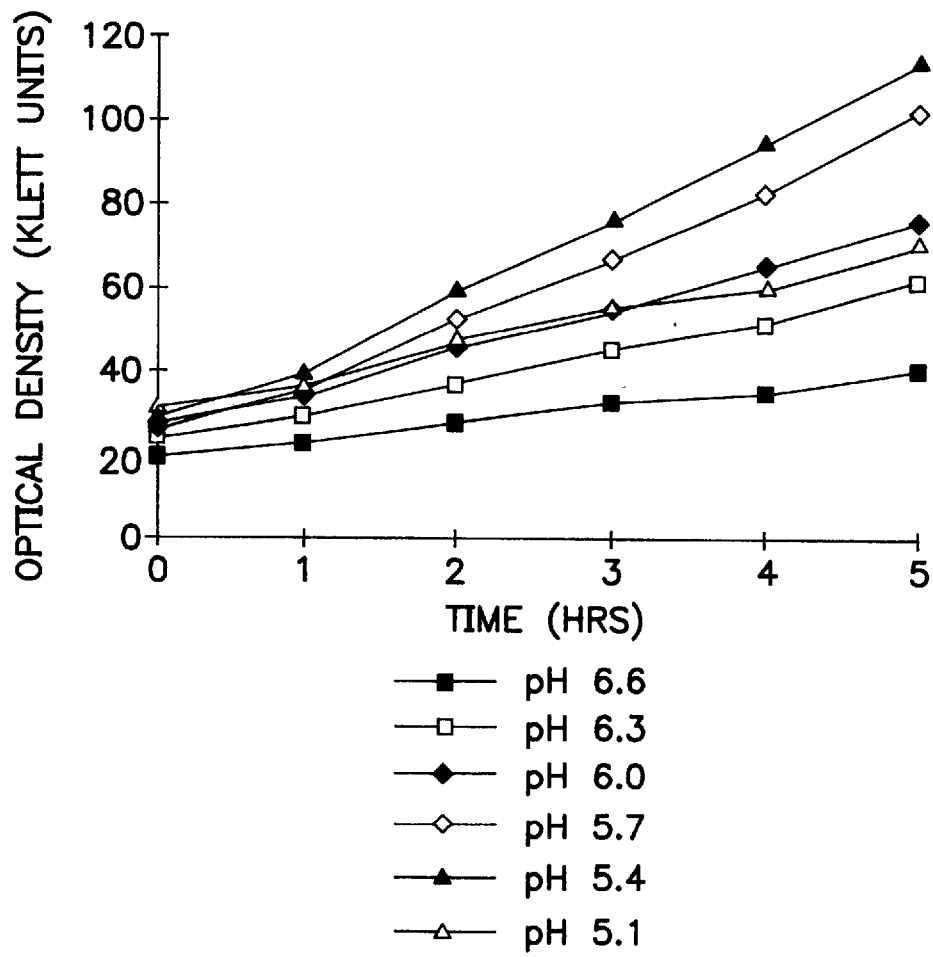
FIG. 5 depicts the effect of pH on cell growth after induction.

The resulting growth rates before and after induction are depicted in FIGS. 4 and 5. The growth rates did not vary significantly before induction. However, the final cell density of at the highest pH tested, 6.6, was approximately 35. The final cell densities increased as the pH of the cultures dropped. The highest cell density of approximately 110 was seen in the pH 5.4 culture. This is more than a four fold increase in cell growth. However, at pH 5.1, the cell growth rate dropped.

Example 6: The Effect of Different Non-Limiting Energy Sources on IFN-β Polypeptide Production These experiments proved that use of glycerol as the effective non-limiting energy source can increase the IFN-β polypeptide production rate.

*E.coli*, strain MM294 cells transformed with pSY2501, described in Example 1, were cultured in the medium, below, with either glycerol, fructose, or glucose as the effective, non-limiting energy source.

Glucose Medium 6.6 mM potassium citrate
35 mM KH$_2$PO$_4$
36 mM (NH$_4$)$_2$SO$_4$
5 mM MgSO$_4$
70 mg/L tryptophan
24 mg/L thiamine
50 mg/L ampicillin
4.7 mL/L BTM (trace elements)
20 g/L glucose
4 mM MgSO$_4$ added at 37 OD 680.

Glycerol and Fructose Media 4.4 mM potassium citrate
35 mM KH$_2$PO$_4$
72 mM (NH$_4$)$_2$SO$_4$
5 mM MgSO$_4$
2 g/L glucose
20 g/L glycerol
30 mM KCl
70 mg/L tryptophan
24 mg/L thiamine
50 mg/L ampicillin
4.7 mL/L BTM (trace elements)

To the fructose culture, 5 mM MgSO$_4$, 15 mM KH$_2$PO$_4$, and 20 mM (NH$_4$)$_2$SO$_4$ were added 40 OD$_{680}$.

To the glycerol culture, 5 mM MgSO$_4$ and 15 mM KH$_2$PO$_4$ were added at 40 OD$_{680}$.

To each culture, 10 mL of PPG antifoam was added and the fermentor was inoculated with 10–20 mg (dry weight) of cells. The fermentation medium was maintained at a pH of 5.7 with 7.4N NH₄OH, except the glucose fed medium which was maintained at pH 5.4. Fifty percent (v/v) glycerol, fructose, or glucose is feed at a 3.5:1 ratio with the ammonium hydroxide. The temperature was maintained at 37° C. The cells were harvested at various time points during the fermentation.

Figure 6:
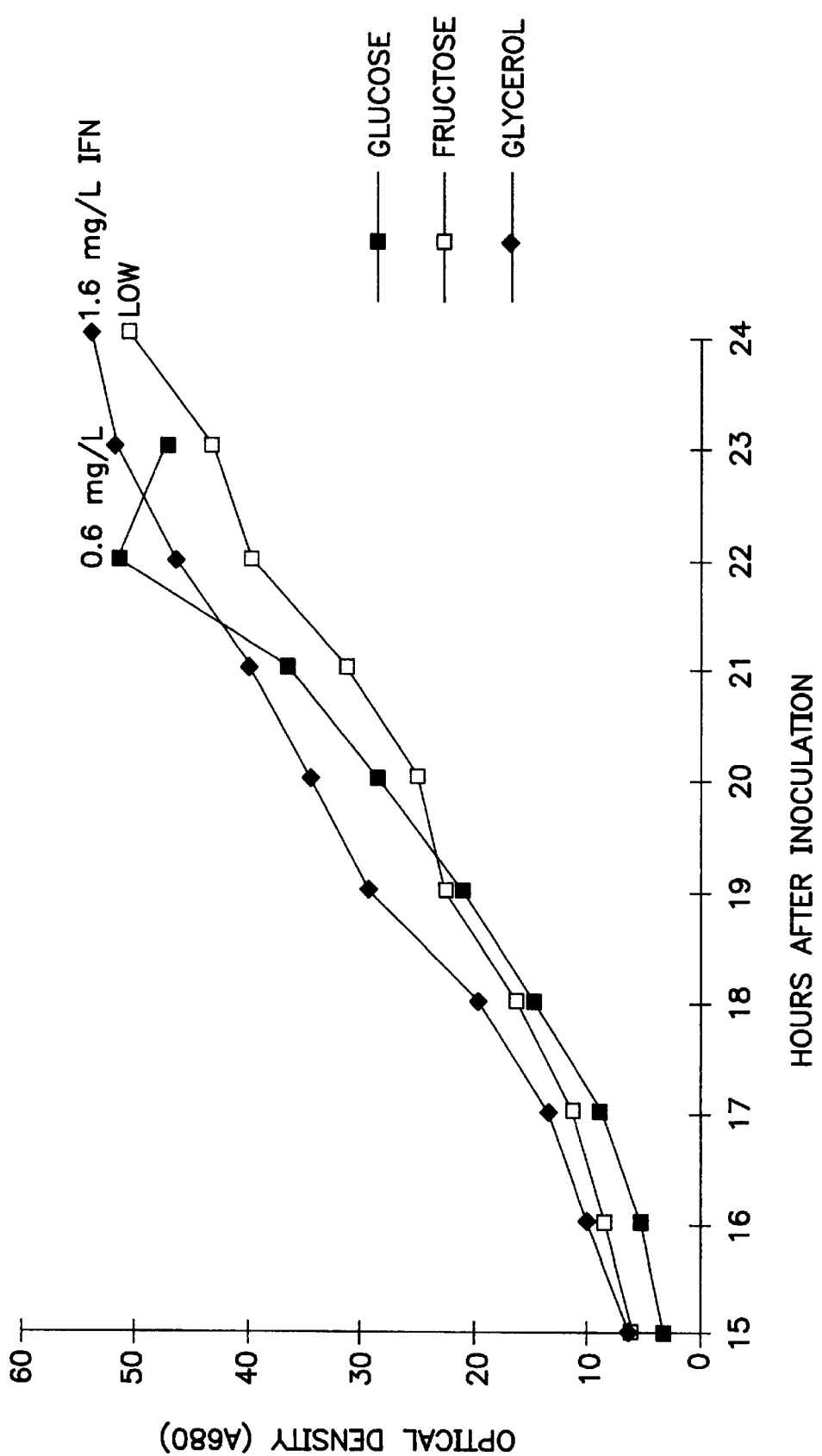
FIG. 6 shows the effect of carbon source on cell growth and polypeptide expression.

Almost no IFN-β polypeptide production was detected for the fructose fermentation. The glycerol fermentation produced 1.6 mg/L of IFN-β polypeptide compared to the glucose fermentation, which only produced 0.6 mg/L. This is approximately a 2.6 fold increase. The results are shown in FIG. 6.

The IFN-β polypeptide concentration was measured by SDS-PAGE analysis with a IFN-β polypeptide standard.

Example 7: The Effect of Temperature on IFN-β Polypeptide Production

These fermentor experiments showed that the IFN-β polypeptide production rates increases as the temperature increases.

*E.coli,* strain MM294 cells transformed with pSY2501, described in Example 1, were cultured in the medium, below, at varying temperatures:

4.4 mM potassium citrate
   26.8 mM KH₂PO₄
   25.9 mM (NH₄)₂SO₄
   48.2 mM NH4H2PO4
   10 mM MgSO₄
   2 g/L glucose
   20 g/L glycerol
   140 mg/L tryptophan
   24 mg/L thiamine
   4.7 mL/L BTM (trace elements)

To the each fermentor, 10 mL of PPG antifoam (manufacturer) was added and the fermentor was inoculated with 10–20 mg (dry weight) of cells.

The fermentation medium was maintained at a pH of 5.7 with 7.4N NH₄OH. Fifty percent (v/v) glycerol is feed at a 3.5:1 ratio with the ammonium hydroxide. The temperature was maintained at 34° or 37° or 40° C.

The growth rates of the different cultures did not vary greatly. However, as the temperature increased, the yield of IFN-β polypeptide compared to total cell protein also increased. At 34° C., 8.5% of the protein produced was IFN-β polypeptide. At 37° C. and 40° C., 10.5% and 13.5%, respectively, of the total protein produced was IFN-β polypeptide. In the control experiment, described in Example 2, only 5.1% of the total protein was IFN-β polypeptide.

Figure 7:
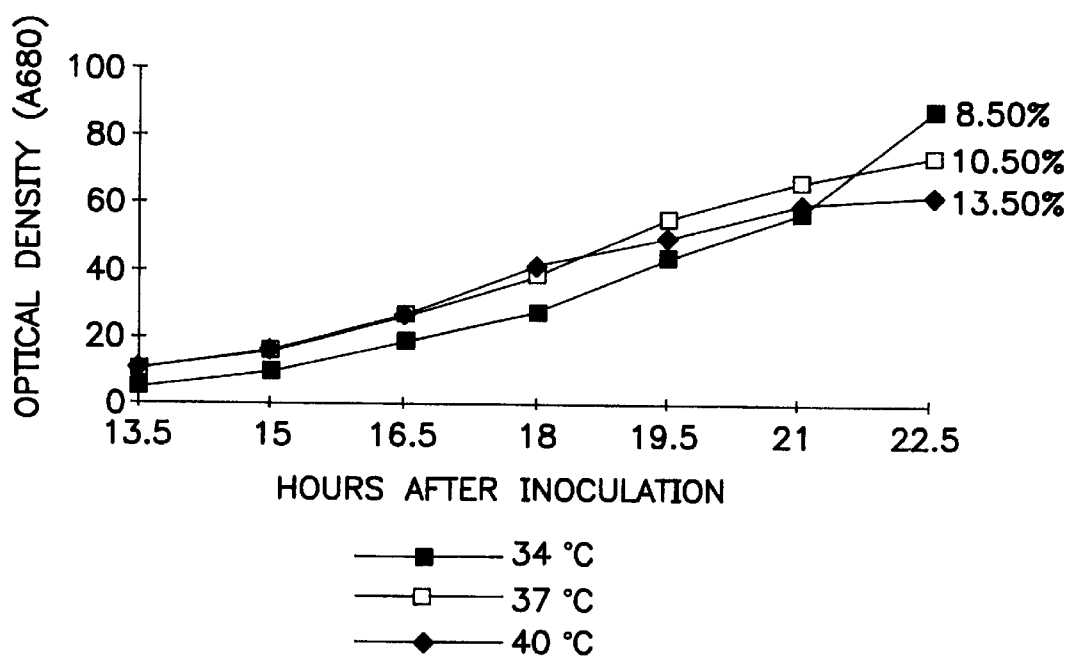
FIG. 7 demonstrates the effect of temperature on cell growth and polypeptide expression.

The IFN-β polypeptide concentration was measured by SDS-PAGE analysis with a IFN-β polypeptide standard. The total protein concentration was assayed by BCA. The data is depicted in FIG. 7.

Example 8: Final Recipe and Culturing Conditions

The following fermentation procedure incorporated low potassium and sodium cation concentrations, low pH, high temperature, and glycerol as the effective non-limiting energy source. The average IFN-β polypeptide production from this fermentation procedure is 5 to 6 fold better than the production of the procedure described in Example 2.

*E.coli,* strain MM294-1 cells transformed with pSY2501, described in Example 1, were the cells used for this fermentation procedure.

For a 10 liters fermentor, first 900 mL of 50% (v/v) glycerol was added to a 2 liters vessel and brought to a final volume of approximately 1.2 liters with deionized (DI) water. To the 2 liters vessel, the following components were added in the order listed. Each component was completely dissolved before adding the next one.

| | |
|---|---|
| Potassium citrate (FW = 306.4) (12.1 g for monohydrate) | 11.5 g |
| BTM | 40 mL |
| Glucose | 17 g |
| KH₂PO₄ (FW = 136.1) | 31.0 g |
| NH₄H₂PO₄ (FW = 115) | 47.1 g |
| (NH₄)₂SO₄ (FW = 132.1) | 29.1 g |
| MgSO₄.7H₂O (FW = 246.5) | 21.0 g |
| Thiamine.HCl | 204 mg |
| L-tryptophan | 1.19 g |

The solution was brought to a final volume of 1.5 liters and sterile filtered. BTM is a trace element mixture. The composition of BTM is as follows:

100 mM FeCl₃
   9.6 mM ZnCl₂
   8.4 nM CoCl₂
   8.3 mM Na₂MoO₄
   6.8 mM CaCl₂
   7.4 mM CuCl₂
   2.5 mM H₃BO₃
in 10% HCl.

This solution was added to a sterilized fermentor containing approximately 7.0 liters of DI water. Next, the solution in the fermentor was brought to a final volume of 9.0 liters with DI water. Ten mL of PPG antifoam was added and the fermentor was inoculated with 10–20 mg (dry weight) of cells.

The fermentation medium was maintained at a pH of 5.7 with 7.4N NH₄OH. Fifty percent (v/v) glycerol was fed at a 3.5:1 ratio with the ammonium hydroxide. Leucine and isoleucine were also fed to the host cells with the glycerol and the base. These amino acids were fed by adding to 26.4 g of isoleucine and 19.7 g of leucine to every 700 mLs of 7.4N NH₄OH. This mixture of base and amino acids was used to maintain the pH of the culture medium. The initial glycerol volume in the feed reservoir should be 1500 mL. The temperature was maintained at 39.5° C. The cells were harvested seven hours after reaching an optical density of 16 $OD_{680}$ units.

A typical fermentation run following these procedures produced an average of ~2.0–2.5 g/L IFN-β polypeptide compared to the control fermentation, described in Example 2, which produced an average of 0.35 g/L. These fermentation conditions produce over 5–6 fold more IFN-β polypeptide than the control fermentation conditions. Further, an average of ~11.5% of the total cell protein, utilizing these procedures, is IFN-β polypeptide compared to an average of ~5.1% in the control fermentation. Thus, the IFN-β polypeptide produced by this procedure has approximately over 2 fold increase of purity.

Deposit Information

The following materials were deposited with the American Type Culture Collection:

| Cell Line | Deposit Date | Accession No. |
|---|---|---|
| *E. coli,* strain MM294-1 transformed with pSY2501 | 18 Nov 1983 | 39517 |

The above materials have been deposited with the American Type Culture Collection, Rockville, Md., under the accession numbers indicated. This deposit will be maintained under the terms of the Budapest Treaty on the International Recognition of the Deposit of Microorganisms for purposes of Patent Procedure. The deposits will be maintained for a period of 30 years following issuance of this patent, or for the enforceable life of the patent, whichever is greater. Upon issuance of the patent, the deposits will be available to the public from the ATCC without restriction.

These deposits are provided merely as convenience to those of skill in the art, and are not an admission that a deposit is required under 35 U.S.C. §112. The sequence of the polynucleotides contained within the deposited materials, as well as the amino acid sequence of the polypeptides encoded thereby, are incorporated herein by reference and are controlling in the event of any conflict with the written description of sequences herein. A license may be required to make, use, or sell the deposited materials, and no such license is granted hereby.

---

What is claimed:

1. A method for producing an interferon-β (IFN-β) polypeptide in *Escherichia coli,* comprising:
    (a) providing an *Escherichia coli* host cell transformed with a vector comprising a sequence encoding an IFN-β polypeptide; and
    (b) culturing the cell under conditions effective to induce production of the IFN-β polypeptide in a medium comprising a concentration of potassium cations no greater than about 75 mM and a concentration of sodium cations no greater than about 40 mM, wherein the pH of the medium is maintained between about 5.4 and about 6.0.

2. The method of claim 1, wherein the concentration of sodium cations is no greater than about 5 mM.

3. The method of claim 2, wherein the concentration of sodium cations is no greater than about 50 $\mu$M.

4. The method of claim 2, wherein the temperature of the medium is maintained between about 34° C. and 42° C.

5. The method of claim 1, wherein the concentration of potassium cations is no greater than about 40 mM.

6. The method of claim 1, wherein the pH is maintained at about 5.7.

7. The method of claim 1, wherein the medium further comprises glycerol wherein the amount and concentration of glycerol does not limit the final cell density.

8. The method of claim 7, wherein the glycerol concentration is between about 2 g/L and about 100 g/L.

9. The method of claim 1, wherein the amino acid sequence of the interferon-β polypeptide is SEQ ID NO:1 and amino acid 17 is a serine.

10. The method of claim 9, wherein the potassium cation concentration is no greater than about 40 mM;

the sodium cation concentration is no greater than about 10 $\mu$M;

the pH is maintained at about 5.7;

the temperature of the medium is maintained at about 39.5° C.; and the medium further comprises glycerol in an amount that does not limit cell density.

\* \* \* \* \*

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 166 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Met Ser Tyr Asn Leu Leu Gly Phe Leu Gln Arg Ser Ser Asn Phe Gln
 1               5                  10                 15
Cys Gln Lys Leu Leu Trp Gln Leu Asn Gly Arg Leu Glu Tyr Cys Leu
            20                  25                 30
Lys Asp Arg Met Asn Phe Asp Ile Pro Glu Glu Ile Lys Gln Leu Gln
         35                  40                 45
Gln Phe Gln Lys Glu Asp Ala Ala Leu Thr Ile Tyr Glu Met Leu Gln
     50                  55                 60
Asn Ile Phe Ala Leu Phe Arg Gln Asp Ser Ser Ser Thr Gly Trp Asn
 65                  70                 75                  80
Glu Thr Ile Val Glu Asn Leu Leu Ala Asn Val Tyr His Gln Ile Asn
                 85                  90                 95
His Leu Lys Thr Val Leu Glu Glu Lys Leu Glu Lys Glu Asp Phe Thr
                100                 105                110
Arg Gly Lys Leu Met Ser Ser Leu His Leu Lys Arg Tyr Tyr Gly Arg
            115                 120                 125
Ile Leu His Tyr Leu Lys Ala Lys Glu Tyr Ser His Cys Ala Trp Thr
        130                 135                 140
Ile Val Arg Val Glu Ile Leu Arg Asn Phe Tyr Phe Ile Asn Arg Leu
145                 150                 155                160
Thr Gly Tyr Leu Arg Asn
                165
```

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA, Synthetic"

( x i ) SEQUENCE DESCRIPTION: SEQ ID NO:2:

```
TATGAGCTAC AAC                                                                                        1 3
```

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "DNA, Synthetic"

( x i ) SEQUENCE DESCRIPTION: SEQ ID NO:3:

```
GCAATTTTCA GAGTCAG                                                                                    1 7
```